United States Patent
Wilt et al.

(10) Patent No.: US 7,512,500 B2
(45) Date of Patent: Mar. 31, 2009

(54) METHOD FOR SENSOR INITIALIZATION IN A STRUCTURAL HEALTH MANAGEMENT SYSTEM

(75) Inventors: Nicholas J. Wilt, Glendale, AZ (US); Steven R. Thompson, Phoenix, AZ (US); Scott Gray, Peoria, AZ (US)

(73) Assignee: Honeywell International, Inc., Morristow, NJ (US)

( * ) Notice: Subject to any disclaimer, the term of this patent is extended or adjusted under 35 U.S.C. 154(b) by 484 days.

(21) Appl. No.: 11/019,691

(22) Filed: Dec. 21, 2004

(65) Prior Publication Data

US 2006/0136359 A1    Jun. 22, 2006

(51) Int. Cl.
    *G06F 3/00* (2006.01)
(52) U.S. Cl. .................... 702/34; 702/35; 702/182; 702/183
(58) Field of Classification Search ............. 702/76, 702/77, 113, 141, 179, 182, 189; 128/630; 340/870.02; 455/3.01
    See application file for complete search history.

(56) References Cited

U.S. PATENT DOCUMENTS

| | | | |
|---|---|---|---|
| 5,682,882 A * | 11/1997 | Lieberman | 600/301 |
| 6,657,552 B2 * | 12/2003 | Belski et al. | 340/870.02 |
| 6,789,030 B1 * | 9/2004 | Coyle et al. | 702/77 |
| 6,961,536 B2 * | 11/2005 | Himmel et al. | 455/3.01 |
| 7,209,859 B2 * | 4/2007 | Zeif | 702/182 |
| 2002/0104083 A1 * | 8/2002 | Hendricks et al. | 725/34 |

* cited by examiner

*Primary Examiner*—Eliseo Ramos Feliciano
*Assistant Examiner*—Felix E Suarez
(74) *Attorney, Agent, or Firm*—Black Lowe & Graham PLLC

(57) ABSTRACT

A method for initializing a chain of non-initialized data collectors is disclosed. The chain of non-initialized data collectors are coupled to a controller. In a first step communication between the controller and each data collector in the chain of non-initialized collectors is disabled, except for an active non-initialized data collector, The active non-initialized collector is coupled to the controller and any remaining non-initialized data collectors. Next, the active non-initialized data collector is initialized by assigning an identification number to the active non-initialized data collectors. The active non-initialized collector becomes an initialized data collector. Then, communication is restored between the initialized data collector and a next active non-initialized data collector in the chain of non-initialized data collectors. The method repeats until all non-initialized data collectors are initialized.

16 Claims, 3 Drawing Sheets

METHOD FOR SENSOR INITIALIZATION IN A STRUCTURAL HEALTH MANAGEMENT SYSTEM

TECHNICAL FIELD

This invention relates to the field of structural health management and more specifically to a method for sensor initialization in a structural health management system.

BACKGROUND

Nondestructive testing is a procedure for determining the quality or characteristics of a structure without permanently altering the structure or the structure's properties. Examples include ultrasonic and radiographic inspection. In the avionics field, nondestructive evaluations of airplane components are done to insure the structural integrity of the airplane. In typical nondestructive testing schemes, a certified inspector performs one or more nondestructive tests at the aircraft. This process may be repeated at regular intervals to monitor the structural health of the aircraft.

While this type of nondestructive testing scheme can be effective, it may have several potential drawbacks. First, the test typically needs to be conducted by trained inspectors, which can incur significant costs, including the potential loss of operational revenue, when having an inspector perform the tests on site. Second, to enable efficient analysis and repetitive comparison over time, a non-subjective decision process driven by inspection data, inspection method parameters, location, decision criteria, and material properties within the context of the structure being inspected may be required. Current inspection approaches may not preserve these components. Although each inspection can be analyzed individually, a collection of inspections may not be analyzed in toto.

To resolve some of the drawbacks of current nondestructive schemes, other structural health management schemes have been developed. In one structural health management technique, ultrasonic transducers can be placed, for example, on the fuselage of the aircraft to be tested. The ultrasonic transducers are then coupled to an onboard testing computer. The testing computer can be used to run nondestructive tests when needed by using the installed ultrasonic transducers.

The above-described system allows for nondestructive testing to be done without having an inspector bring equipment to the aircraft. Additionally, the automated inspection and determination of the state of the inspected material preserves accurate location data, as well as the associated data used to perform the inspection and make the determination. This allows multiple self-referential inspections of an area over an extended period of time, enabling correlation, trending and other sophisticated analysis of the inspection data across vehicles and over time.

Sensor data collectors can be used to collect the data gathered by the sensors. However, when using sensors data collectors that are interconnected on the same data bus, unless the sensor data collectors have some type of identification, the sensor data collectors can not correctly respond to a controller or processor. What is needed is a method for sensor data collector initialization.

BRIEF SUMMARY

In an exemplary embodiment of the present a method for initializing a chain of non-initialized data collectors is disclosed. The chain of non-initialized data collectors are coupled to a controller. In a first step communication between the controller and each data collector in the chain of non-initialized collectors is disabled, except for an active non-initialized data collector, The active non-initialized collector is coupled to the controller and any remaining non-initialized data collectors. Next, the active non-initialized data collector is initialized by assigning an identification number to the active non-initialized data collectors. The active non-initialized collector becomes an initialized data collector. Then, communication is restored between the initialized data collector and a next active non-initialized data collector in the chain of non-initialized data collectors. The method repeats until all non-initialized data collectors are initialized.

In another exemplary embodiment, a data collection apparatus is disclosed. The apparatus comprises two or more serially connected data collectors coupled to a controller. Each data collector comprises a data input, a data output and a switch coupling the data input and data output. The switch is configured to isolate the data input from the data output. The controller is coupled to the data input of a first data collector of the two or more data collectors.

In another embodiment, the controller is configured to send a request to open the switch of the first data collector processor. The request is sent to a processor in the first data collector. The processor is configured to send an open command to the switch of the first data collector.

BRIEF DESCRIPTION OF THE DRAWINGS

The present invention will hereinafter be described in conjunction with the following drawing figures, wherein like numerals denote like elements, and.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description. While the invention is discussed in an avionics embodiment, the teachings of the present invention are applicable to many different fields of endeavor.

Figure 1:
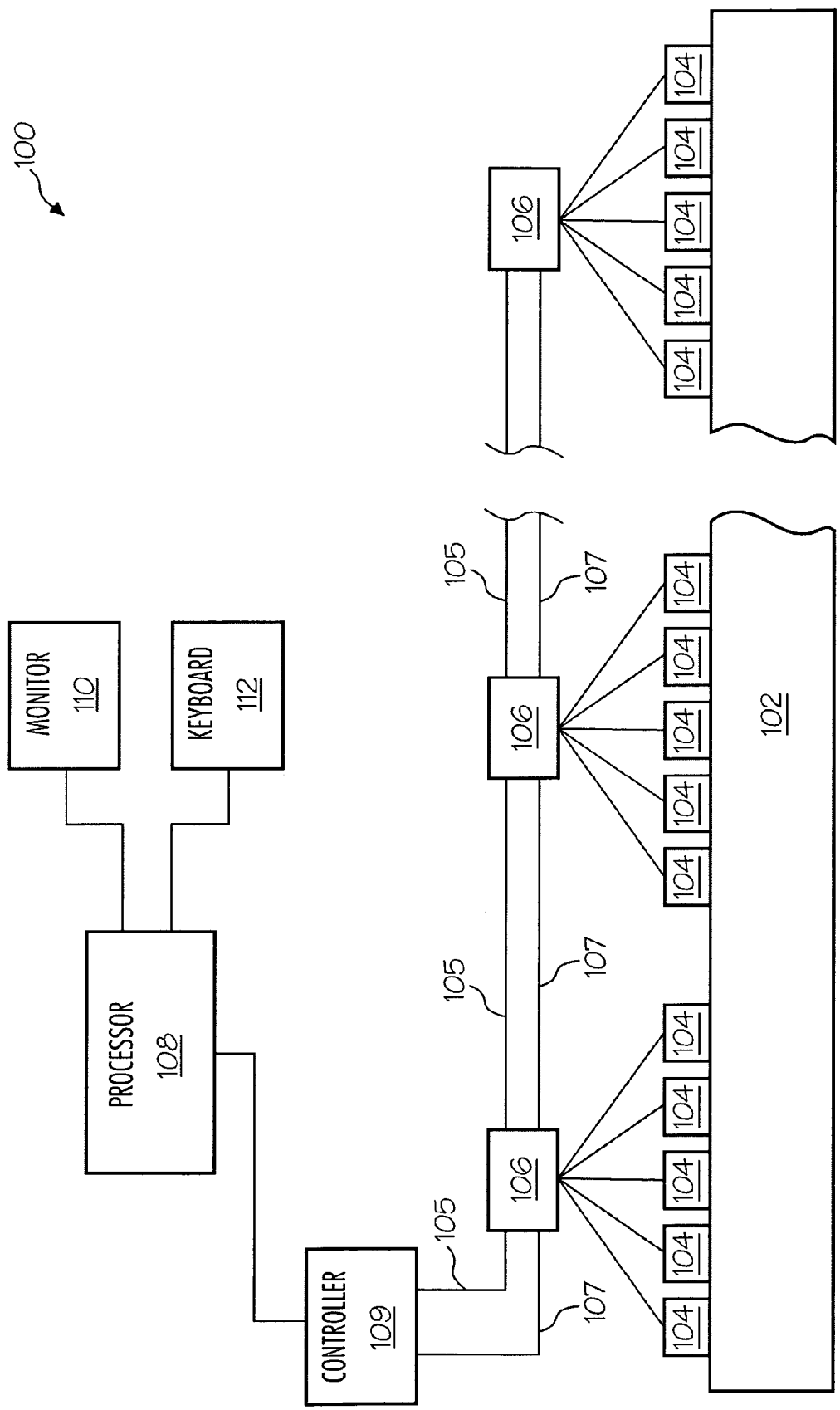
FIG. 1 illustrates an exemplary structural health monitoring system in accordance with the teachings of the present invention.

FIG. 1 illustrates an exemplary structural health management system 100 in accordance with the teachings of the present invention. Structural health management system 100 includes a plurality of sensors 104 coupled to one or more sensor data collectors (SDCs) 106. Each sensor 104 is mounted to a structure 102 to be tested. In the embodiment as shown in FIG. 1, each SDC is coupled to each other by a data bus 107 and a power line 105. The SDCs 106 are coupled to a controller 109 via the data bus 107 and the power line 105. The controller 109 couples to at least one structural health monitoring processor 108. Various inputs and outputs can be provided to structural health monitoring processor 108. For example, processor 108 can be coupled to various input/output devices including a display 110, a keyboard 112 and the like.

Sensor 104 can be an ultrasonic transducer that converts electrical signals into mechanical vibrations and mechanical vibrations into electrical signals. In this embodiment, sensor 104 converts electricity into mechanical vibrations that propagate waves in the structure 102 to which the sensor 104 is coupled through elastic deformation (known as elastic waves). The propagated waves interact with various features within the structure 102 such as flaws or defects. The sensor 104 can also receive transmitted and reflected waves and convert the mechanical vibrations caused by these waves into electrical signals. These electrical signals can then be analyzed to determine if there are any flaws or defects in the structure 102.

The amount of time it takes for a wave to travel between two sensed locations is known as the time-of-flight. In addition to the time-of-flight, signal amplitude, and signal energy of an elastic wave received by a sensor 104 can be used in models to predict the underlying damage state of the area traversed by the propagated elastic wave. Various features within the structure 102, such as fatigue cracks or other structural flaws, can be identified and located based on these values obtained from data collected by sensor 104 and others.

While many different designs for sensors 104 exist, in one embodiment, sensor 104 is a piezoelectric transducer. Piezoelectric transducers produce mechanical vibrations when an electric signal is applied and produce electrical signals when receiving mechanical vibrations. Typically, piezoelectric transducers use piezoelectric ceramics that can be engineered to produce different wave modes.

Different types of waves induced by piezoelectric transducers can be used in nondestructive testing. In an embodiment of the present invention, the sensor 104 produces Lamb waves in structure 102. Lamb waves propagate throughout the entire thickness of plate-like structures, such as the composite material used for the skin of an aircraft. Lamb waves are a form of guided elastic waves distinct from the bulk waves used in a traditional ultrasonic approach. Lamb waves traverse along the plate-like structures while exciting material throughout the plate's thickness. As a consequence, the use of Lamb waves allows for distributed sensors schemes to examine the composite plate-like structure over a given area without the need to scan the transducers over certain areas.

SDCs 106, in one embodiment of the present invention, collect data from the sensors 104 in the form of electrical signals and send the data to processor 108 for evaluation. In another embodiment, SDCs 106 collect data and can perform some analysis on the data prior to sending the data to the processor 108. By providing multiple SDCs 106, if one SDC 106 was to fail, or otherwise become inoperative, the entire structural health management system 100 would continue to operate. Additionally, in one embodiment, SDCs 106 accept multiple sensor inputs and provide a single high speed data output, resulting in a reduction in the amount of wiring required between the sensors 104 and the processor 108. In one embodiment, SDCs 106 are arranged as a chain of serially coupled SDCs 106.

Processor 108 can receive data from the sensors 104, either directly or via SDCs 106. Processor 108 can also process the data to evaluate the structural health of the structure 102. Processor 108 can also receive data from sensors 104 and perform damage assessment analysis. Processor 108 can be a commercial off the shelf processor and any components necessary to allow processor 108 to process data. Processor 108 can couple to input/output devices such as the display 110 and keyboard 112.

Controller 109 provides commands to the SDCs 106 indicating which sensors to fire. Controller 109 can issue commands to the SDC 106 to enable power or data communication to other SDCs 106. In one embodiment, the functionality of controller 109 can be provided by processor 108.

In one embodiment of the present invention, one controller can be coupled to multiple SDCs 106. For example, in a chain of SDCs 106, a controller 109 can connect directly to a first SDC 106 in the chain of SDCs 106 with the other SDCs 106 coupled serially after the first SDC 106 in the chain. In one embodiment, the controller 109 can communicate with each of the SDCs 106 coupled to the controller 109 by using an identification number uniquely associated with each of the SDCs 106 in a group. The identification numbers can be assigned by the controller 109 to each of the SDCs 106 coupled to the controller 109.

Structure 102 can be any one of numerous types of material of interest to be tested. In one embodiment, structure 102 is a composite material used for the skin of an aircraft. In one exemplary embodiment, structure 102 is a plate-like composite material such as the material used to form modern aircraft skin.

Prior to performing any analysis using sensors 104, the SDC 106 is initialized so controller 109 can properly address the correct SDC 106 when needed. A method for initializing SDCs 106 is illustrated in conjunction with FIGS. 2-3.

Figure 2:
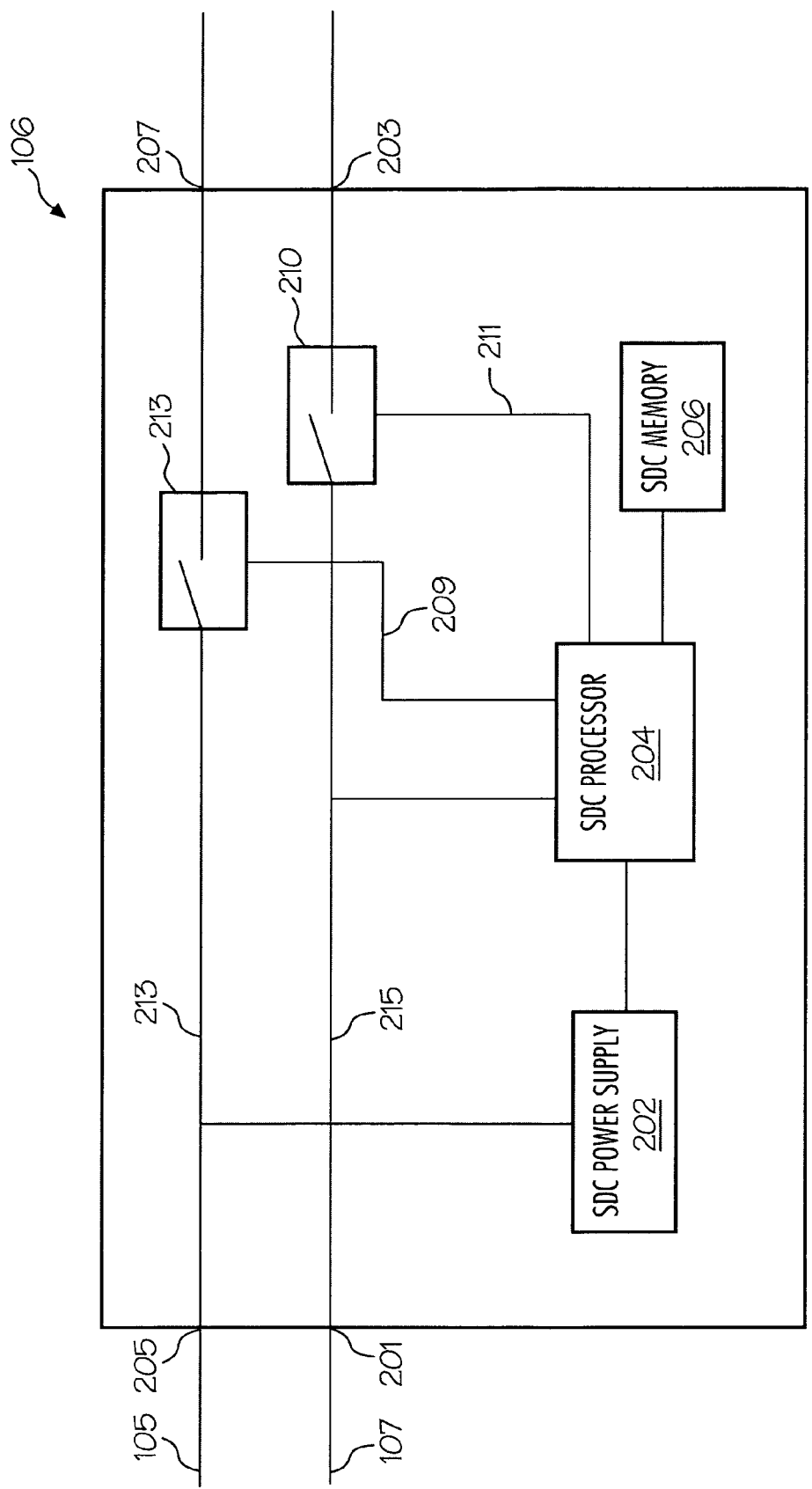
FIG. 2 is a block diagram of a sensor data collector in accordance with the teachings of the present invention.

An exemplary SDC 106 is shown in FIG. 2. SDC 106 comprises a data input 201, a data output 203, a power input 205 and a power output 207. Data bus 107 couples to the data input 201, and exits the SDC 106 at data output 203. Power line 105 couples to the power input 205 and exits the SDC 106 at the power output 207.

Internal to SDC 106, an internal power line 213 couples to a SDC power supply 202, which provides power to the other components internal to SDC 106. SDC processor 204 receives data from data bus 107 over an internal data line 215. An SDC memory 206 can be coupled to the SDC processor 204. The power output 207 can be decoupled from the power line 105 via a power switch 208. Also, data output 203 can be decoupled from data bus 107 via a data switch 210.

In one embodiment, power switch 208 is under control of SDC processor 204 via a power control line 209 and data switch 210 is under the control of SDC processor 204 via a data control line 211. While the exemplary SDC 106 illustrated in FIG. 2 includes both the power switch 208 and the data switch 210, in one embodiment of the present invention only the power switch 208 or the data switch 210 need be provided.

SDC processor 204 along with SDC memory 206, typically under the command of controller 109, controls the operation of SDC sensors 104. SDC processor 204 can collect data for storage in SDC memory 206, for local processing, or for forwarding to processor 108.

The power switch 208 allows each SDC 106 to disable or enable power to SDCs 106 that are coupled after the power output 207. In one embodiment power switch 208 can be disabled using a command sent by SDC processor 204 via power control line 209. Similarly, data switch 210 allows the SDC 106 to enable or disable communication over the data bus 107 to all SDCs 106 coupled after the data output 203 of the current SDC 106. In one embodiment, data communication can be disabled to data output 203 by opening the data switch 210 using a command sent by SDC processor 204 via data command line 211. When the power switch 208 in the SDC 106 is open, any downstream SDC 106 will not receive power. Similarly, if the data switch 210 is open, thus decoupling any downstream SDC 106 from the data output 203 of the SDC 106 having the open data switch 210; the downstream SDCs 106 will not be able to receive data. Typically the SDC processor 204 sends commands to the data switch 210 and the power switch 208 under the control of controller 109.

Figure 3:
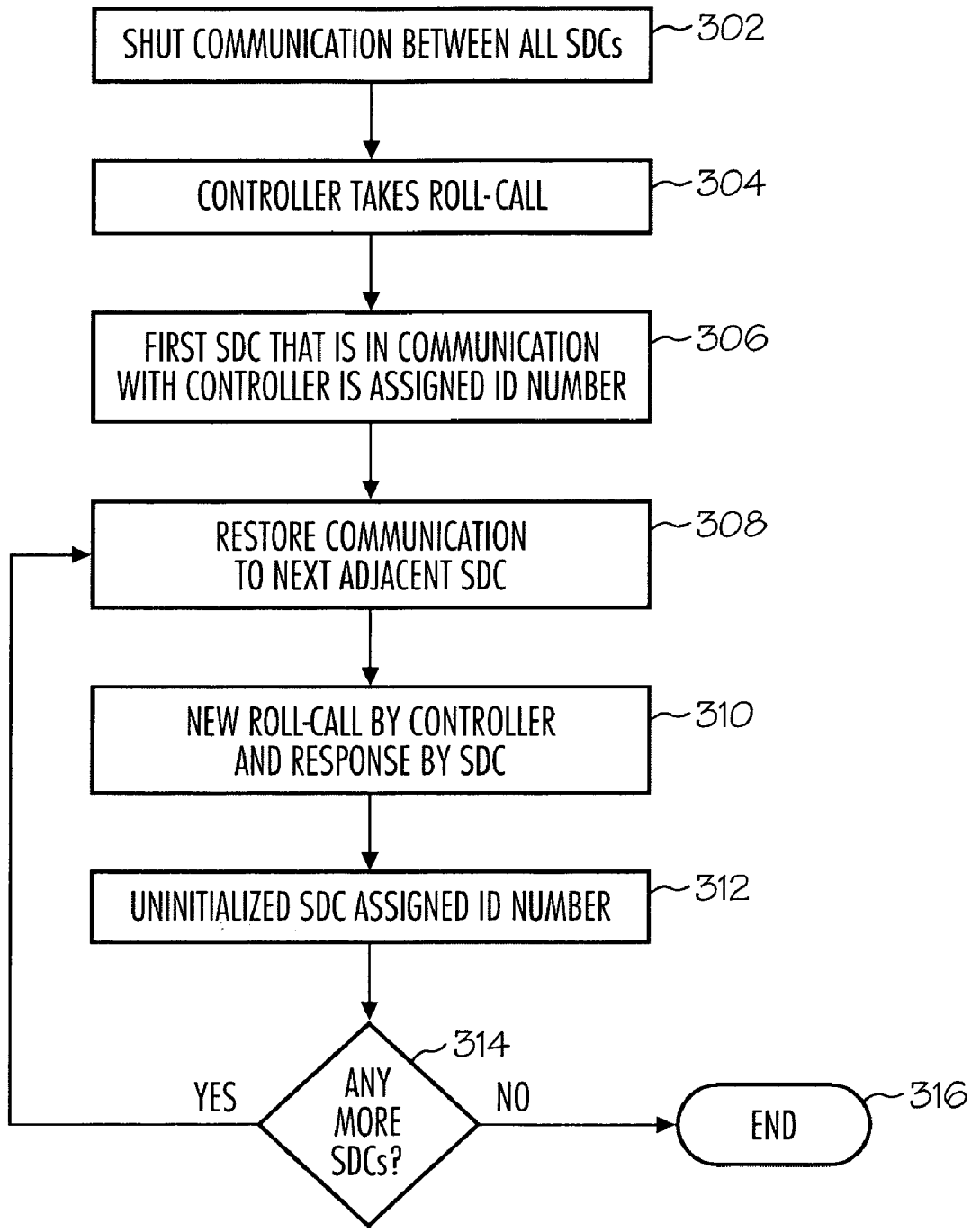
FIG. 3 is a flowchart of a method for initializing sensor data collectors in a structural health management system in accordance with the teachings of the present invention.

FIG. 3 is a flowchart illustrating an exemplary method for initiating a plurality of connected SDCs 106 coupled to the controller 109 in accordance with the teachings of the present invention. In step 302, all SDCs 106 disable the power line 105 or data bus 107 connection to downstream SDCs 106. This is done by opening either power switch 208 or data switch 210 in each SDC 106. The switches can be opened upon a command from the system controller 109 as a default upon an initial powering up and/or a default following a reset of the system.

Next, in step 304, the controller takes a roll-call of the SDCs 106. In a typical embodiment a roll call is sent as a query to the SDCs 106 to reply to the controller 109. Initially, all but one of the SDCs 106 are unable to respond because the SDCs 106 either are not powered by power line 105 or are not linked over the data bus 107 (or, in one embodiment, neither powered over power line 105 nor linked over data bus 107). The only SDC 106 that can respond is the first SDC 106 coupled to the system controller 109. Then, in step 306, the first SDC 106 that is both powered and in communication with the system controller 109 in the chain responds to the roll call and the system controller 109 assigns the SDC 106 an identification number which is stored in SDC memory 206. The identification number can be any symbology, including electronic representations thereof, that allows the controller 109 to uniquely identify the SDC 106.

Once the first SDC 106 receives an identification number, the system controller commands the SDC 106 to enable the power line 105 or data bus 107 of the newly initialized SDC 106 by closing power switch 208 or data switch 210. Then, in step 308, the system controller 109 again performs a roll-call. Any SDC 106 that has already been assigned an identification number does not reply. Of course, any SDC 106 that is not currently connected to the power line 105 or data bus 107 can not reply. Thus, only one SDC 106 can reply and that is the next SDC in line after the SDC 106 that has just been assigned an identification number. In step 310, the SDC 106 replies and in step 312, is assigned an identification number for storage in SDC memory 206.

Then, in step 314, it is determined if there are any more SDCs 106 that have not been assigned an identification number. If there are more SDCs 106 to be assigned an identification number, the process repeats steps 308 to 314. After all SDCs 106 have been assigned an identification number, the method ends at step 316.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. A method for initializing a chain of non-initialized data collectors, the chain of non-initialized data collectors coupled to a controller, and each data collector in the chain coupled to communicate with one or more other data collectors, the method comprising:

a) disabling comunication between each data collector in the chain of non-initialized data collectors;
b) initializing a first active non-initialized data collector, the first active non-initialized data collector coupled directly to the controller, by assigning an identification number to the first active non-initialized data collector by the controller in response to a first roll-call of the controller, the identification number stored in a memory of the first active non-initialized data collector;
c) restoring communication between the controller and a next non-initialized data collector in the chain of non-initialized data collectors;
d) initializing the next non-initialized data collector in the chain of non-initialized data collectors by assigning an additional identification number by the controller in response to an additional roll-call of the controller, the additional identification number stored in a memory of the next non-initialized data collector; and
e) repeating steps c and d for each non-initialized data collector.

2. The method of claim 1 wherein the step of disabling communication further comprises disabling a power line between each data collector.

3. The method of claim 1 wherein the step of disabling communication further comprises disabling a data bus between each data collector.

4. The method of claim 1 wherein the step of restoring communications further comprises closing a power switch in one of the chain of data collectors which initialized allows power to flow to the next adjacent data collector.

5. The method of claim 1 wherein the step of restoring communications further comprises closing a data switch in one of the chain of data collectors which initialized allows data to flow to the next adjacent data collector.

6. A method for operating a structural health monitoring system, comprising:

initializing a chain of serially connected data collectors by disabling communication between each data collector in the chain of data collectors, initializing a first data collector by assigning an identification number by a controller in response to a first roll-call of the controller, and restoring communication and initializing each remaining data collector of the chain of data collectors by the controller in response to each of a plurality of additional roll-calls of the controller, each remaining data collector initialized in sequential order until all data collectors are initialized;

sending a command to fire one or more sensors mounted on a test material, the sensors coupled to at least one of the data collectors; and receiving data collected by the one or more sensors.

7. The method of claim 6 wherein the step of disabling communication further comprises disabling a power line between each data collector.

8. The method of claim 6 wherein the step of disabling communication further comprises disabling a data bus between each data collector.

9. The method of claim 6 wherein the step of initializing further comprises storing the identification number in a memory.

10. The method of claim 6 wherein the step of restoring communication and initializing further comprises closing a power switch of an initialized data collector to allow power to flow to a next non-initialized data collector.

11. The method of claim 6 wherein the step of restoring communication and initializing further comprises closing a switch of an initialized data collector to allow data to flow to a next non-initialized data collector.

12. A data collection system, comprising:
- a chain of non-initialized data collectors, each data collector in the chain coupled to communicate with one or more other data collectors; and
- a controller coupled to the chain of non-initialized data collectors, the controller configured for:
  - a) disabling communication between each data collector in the chain of non-initialized data collectors,
  - b) initializing a first active non-initialized data collector, the first active non-initialized data collector coupled directly to the controller, by assigning an identification number to the first active non-initialized data collector by the controller in response to a first roll-call of the controller, the identification number stored in a memory of the first active non-initialized data collector,
  - c) restoring communication between the controller and a next non-initialized data collector in the chain of non-initialized data collectors
  - d) initializing the next non-initialized data collector in the chain of non-initialized data collectors by assigning an additional identification number by the controller in response to an additional roll-call of the controller, the additional identification number stored in a memory of the next non-initialized data collector, and
  - e) repeating steps c and d for each non-initialized data collector.

13. The system of claim 12 wherein the controller is further configured for disabling a power line between each data collector.

14. The system of claim 12 wherein the controller is further configured for disabling a data bus between each data collector.

15. The system of claim 12 wherein the controller is further configured for closing a power switch in one of the chain of data collectors which initialized allows power to flow to the next adjacent data collector.

16. The system of claim 12 wherein the controller is further configured for closing a data switch in one of the chain of data collectors which initialized allows data to flow to the next adjacent data collector.

\* \* \* \* \*